(12) United States Patent
Shalaby

(10) Patent No.: US 7,348,364 B2
(45) Date of Patent: *Mar. 25, 2008

(54) SEGMENTED COPOLYESTERS AS COMPLIANT, ABSORBABLE COATINGS AND SEALANTS FOR VASCULAR DEVICES

(75) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 571 days.

This patent is subject to a terminal disclaimer.

(21) Appl. No.: 10/693,360

(22) Filed: Oct. 24, 2003

(65) Prior Publication Data

US 2004/0109892 A1 Jun. 10, 2004

Related U.S. Application Data

(60) Provisional application No. 60/422,653, filed on Oct. 31, 2002.

(51) Int. Cl.
*A61K 47/00* (2006.01)

(52) U.S. Cl. .............................. 514/772.1; 514/772.3; 977/788

(58) Field of Classification Search ...................... None
See application file for complete search history.

(56) References Cited

U.S. PATENT DOCUMENTS 5,225,521 A * 7/1993 Spinu .......................... 528/354
5,713,920 A * 2/1998 Bezwada et al. ............ 606/230
5,951,997 A * 9/1999 Bezwada et al. ............ 424/426
6,211,249 B1* 4/2001 Cohn et al. ............... 514/772.1
6,309,669 B1* 10/2001 Setterstrom et al. ........ 424/486
6,447,796 B1* 9/2002 Vook et al. .................. 424/422
6,462,169 B1 10/2002 Shalaby
7,097,907 B2* 8/2006 Bennett et al. ........... 428/423.1

OTHER PUBLICATIONS

Tian et al. "Macromolecular engineering of polyactones and polylactides. Synthesis of star-branched aliphatic polyesters bearing various functional end groups" Macromolecuets, 1994, 27, pp. 4134-4144.*

Bennett et al., Initial Biocompatibhility studies of a novel degradable polymeric bone substitute that hardens in situ Bone, Jul. 19,1996, 1 Supplement, pp. 101S-107S. □□.*

Helminen, A. "Branched and crosslinked resorbably polymers based on lactic acid, lactide and eta-caprolactone" Dec. 2003.*

* cited by examiner

*Primary Examiner*—Michael P. Woodward
*Assistant Examiner*—Eric E. Silverman
(74) *Attorney, Agent, or Firm*—Leigh P Gregory

(57) ABSTRACT

Disclosed are absorbable sealants or coatings for biomedical devices which are formulated from a segmented copolyester having a molecular weight of more than 5 kDa, a glass transition temperature of less than 35° C., and low degree of crystallinity evidenced by a heat of fusion of less than 25 J/g.

9 Claims, No Drawings

SEGMENTED COPOLYESTERS AS COMPLIANT, ABSORBABLE COATINGS AND SEALANTS FOR VASCULAR DEVICES

This application claims the benefit of prior provisional application U.S. Ser. No. 60/422,653, filed Oct. 31, 2002.

FIELD OF THE INVENTION

The invention relates to improving the biocompatibility of vascular devices, including vascular grafts and endovascular grafts through using segmented copolyesters, which may be carboxyl-bearing, as compliant, absorbable coatings and sealants of these devices.

BACKGROUND OF THE INVENTION

It is well acknowledged that the biocompatibility requirements of successful blood contacting devices exceed those expected of those interfacing with most biological tissues because of the more complex interaction of blood components with these devices. Among the most important types of blood contacting devices, which are noted for their critical functional requirements are synthetic vascular grafts, endovascular stent grafts, and endovascular stents.

Synthetic vascular grafts made primarily of expanded polytetraethylene (E-PTFE) and woven or knitted polyethylene terephthalate (PET) are most commonly used. Synthetic vascular grafts implanted as large vessel replacements have achieved a reasonable degree of success. However, medium- and small-diameter prostheses (less than 6 mm in diameter) loss of patency within several months after implantation is more acute. Graft failure due to thrombosis or intimal hyperplasia with thrombosis is primarily responsible for failure within 30 days after implantation. Intimal hyperplasia formation is the reason for failure within 6 months after surgery. Shortly after implantation, a layer of fibrin and fibrous tissue covers the intimal and outer surface of the prosthesis, respectively. The fibrin is then replaced by a layer of fibroblasts referred to as neointima. In the latter stages, neointimal hyperplasia formation takes place and ultimately results in the occlusion of the vessel in small-diameter grafts. Events leading to occlusion have been related to less than optimal chemical and/or mechanical biocompatibility of the graft-surface and discontinuity of the mechanical properties across the anastomotic site, due to differences in mechanical compliance between the natural vessel and synthetic graft. Accordingly, most of the prior art on synthetic vascular grafts dealt with improving the graft compliance and/or modifying its luminal surface to intervene with events leading to occlusion. However, most, if not all, efforts have been associated with limited success in the small- and medium-diameter grafts. Other unsolved problems of synthetic vascular grafts which require serious attention to optimize their performance include: (1) bleeding at suture needle holes; (2) blood leakage through the graft walls; and (3) infection due to contamination during surgery. These unsolved problems and consistent needs for improving the biocompatibility at the blood-graft interface justified the exploration of the novel sealants and coatings for synthetic grafts subject of this invention. In effect, certain aspects of the present invention deal with similar complications encountered in endovascular stent grafts. Equally important is the fact that most of the events leading to graft occlusion contribute to the failure of endovascular stents placed in the blood vessel to prevent restenosis following angioplasty. A key factor leading to the functional failure of endovascular stents is manifested in post-operative restenosis due, in part, to smooth muscle cell proliferation across the stent. And certain components of the present invention deal with novel corrective measures to stent functional failure and restenosis. Accordingly, the present invention deals with sealants and coatings for synthetic vascular grafts, and endovascular stent grafts that (1) improve the mechanical and barrier properties of vascular grafts; (2) minimize or eliminate events leading to functional failure of endovascular stent grafts and different types of conduit stabilizing stents; (3) are designed to release necessary bioactive agents which prolong the functional performance of the specific device; and/or (4) provide a timely release of antimicrobial agents to prevent and/or treat infection.

SUMMARY OF THE INVENTION

The present invention deals with absorbable polymeric sealants and coating for vascular devices comprising compliant, segmented copolyesters and polyether-esters that may carry carboxylic groups for ionic conjugation with basic bioactive agents for improved functional performance in the biologic environment, including biocompatibility and preventing leakage and infection. The coating and sealant can be used specifically in conjunction with vascular grafts, endovascular stent grafts, and different types of conduit stabilizing stents.

Accordingly, the present invention is directed to an absorbable sealant for biomedical devices which is a segmented copolyester having a molecular weight of more than 5 kDa, a glass transition temperature of less than 35° C., and low degree of crystallinity evidenced by a heat of fusion of less than 25 J/g. Specifically, the present inventive composition may be employed as a coating or sealant for a variety of biomedical devices such as synthetic vascular grafts, endovascular stent grafts, and conduit stabilizing stents.

In one embodiment, the segmented copolyester of the present invention is made by a process which requires reacting at least one cyclic monomer such as trimethylene carbonate, ε-caprolactone, p-dioxanone, glycolide, lactide, or 1,5-dioxepan-2-one with a polyhydroxy compound, thereby forming an amorphous, polyaxial polymeric initiator, and end-grafting at least one cyclic monomer such as trimethylene carbonate, ε-caprolactone, p-dioxanone, glycolide, lactide, or 1,5-dioxepan-2-one onto the polyaxial initiator.

In another embodiment, the segmented copolyester of the present invention is made by a process which requires end-grafting a polyalkylene succinate with at least one cyclic monomer such as trimethylene carbonate, ε-caprolactone, p-dioxanone, glycolide, lactide, or 1,5-dioxepan-2-one.

In yet another embodiment, the segmented copolyester of the present invention is made by a process which requires end-grafting a polyalkylene glycol with at least one cyclic monomer such as trimethylene carbonate, ε-caprolactone, p-dioxanone, glycolide, lactide, or 1,5-dioxepan-2-one.

In at still further embodiment, the segmented copolyester of the present invention is made by a process which requires end-grafting a block copolymer of polyethylene glycol and polypropylene glycol with at least one cyclic monomer such as trimethylene carbonate, ε-caprolactone, p-dioxanone, glycolide, lactide, or 1,5-dioxepan-2-one.

Alternatively, the segmented copolyester is a polyether-ester.

It is also within the scope of the present invention for the segmented copolyester to include pendant carboxyl-bearing side groups. Such carboxyl-bearing copolyester is may be made by a process which includes the steps of reacting a segmented copolyester with maleic anhydrid under free-radical conditions, thereby introducing at least one anhydride group per chain, and hydrolyzing the anhydrid-bearing copolyester, thereby forming succinic acid based side groups. For this embodiment it is preferred that the segmented copolyester is a polyether-ester. Such carboxyl-bearing segmented copolyester may be ionically conjugated with a basic bioactive agent such as an antithrombotic drug.

Generally, any segmented copolyester in accordance with the present invention may be admixed with a further polyether ester, the further polyether ester having pendant carboxyl-bearing side groups and ionically conjugated with a basic bioactive agent, wherein the segmented copolyester and the further polyether ester are mixed at a ratio of between about 9:1 and about 2:8. As such, it is preferred that the further polyether ester is a liquid at room temperature and that the further polyether-ester is made by a process which requires end-grafting a liquid polyethylene glycol with trimethylene carbonate and glycolide.

Generally, the present absorbable sealant may be formulated with at least one bioactive agent such as an anticoagulant agent, an antiproliferative agent, an antithrombotic agent, an anti-inflammatory agent, an antineoplastic agent, an antiangiogenic agent, or an antibiotic agent.

The present invention is also directed to an absorbable sealant which is an ionic conjugate made by a process which requires reacting a basic bioactive agent such as an anticoagulant agent, an antiproliferative agent, an antithrombotic agent, an anti-inflammatory agent, an antineoplastic agent, an antiangiogenic agent, or an antibiotic agent with an absorbable, carboxyl-bearing polyester having a molecular weight of less than about 10 kDa.

The present invention is also directed to an absorbable coating which is an ionic conjugate made by a process which requires reacting a basic bioactive agent such as an anticoagulant agent, an antiproliferative agent, an antithrombotic agent, an anti-inflammatory agent, an antineoplastic agent, an antiangiogenic agent, or an antibiotic agent with an absorbable, carboxyl-bearing polyester having a molecular weight of less than about 10 kDa.

The present invention is also directed to an absorbable sealant which is a blend of a solid matrix of a carboxyl-bearing copolyester and a liquid carboxyl-bearing polyether-ester, the blend further including at least one basic bioactive agent such as an anticoagulant agent, an antiproliferative agent, an antithrombotic agent, an anti-inflammatory agent, an antineoplastic agent, an antiangiogenic agent, or an antibiotic agents, wherein the basic bioactive agent is at least partially conjugated with the carboxyl groups of at least one of the solid matrix and the liquid polyether-ester.

DETAILED DESCRIPTION OF THE PREFERRED EMBODIMENTS

In general, this invention deals with absorbable, segmented copolyesters having a molecular weight of more than 5 kDa, a glass transition temperature of less than 35° C., and low degree of crystallinity associated with a heat of fusion of less than 25 J/g for (1) coating or sealing synthetic vascular grafts and stent grafts, particularly those made of E-PTFE, PET and segmented polyurethanes (S-PU), and (2) coating different types of conduit stabilizing stents. A specific aspect of this invention deals with an absorbable coating and sealant comprising a polyaxial segmented copolyester made by the copolymerization of two or more cyclic monomer such as trimethylene carbonate, $\epsilon$-caprolactone, p-dioxanone, glycolide, lactide, 1,5-dioxepan-2-one. The polyaxial segmented copolyesters were prepared using similar procedures to those described in U.S. Pat. No. 6,462,169. Another aspect of the invention deals with improving the sealant or coating barrier properties that entails treating the polyaxial, segmented copolyester on the vascular device with a diisocyanate, such as diisocyanatohexane, to crosslink said polymers. Another specific aspect of this invention deals with an absorbable coating and sealant comprising a linear segmented copolyester made by end-grafting a polyalkylene glycol, such as polyethylene glycol or a block of polyethylene glycol and polypropylene glycol with one or more cyclic monomer such as trimethylene carbonate, $\epsilon$-caprolactone, p-dioxanone, glycolide, lactide, 1,5-dioxepan-2-one. Another specific aspect of this invention deals with an absorbable coating and sealant comprising a segmented copolyester made by end-grafting a polyalkylene succinate such as polyethylene succinate and polytrimethylene succinate with one or more cyclic monomer such as trimethylene carbonate, $\epsilon$-caprolactone, p-dioxanone, glycolide, lactide, 1,5-dioxepan-2-one. Another aspect of this invention deals with an absorbable coating and sealant comprising the aforementioned groups of segmented copolyesters having one or more succinic acid side groups introduced onto the main chain of copolyesters by a process referred to herein as C-succinylation, which entails (1) grafting the segmented copolyester with maleic anhydride (a process referred to herein as C-succinylation, to form a C-succinylated product) in the presence of a free-radical initiator such as benzoyl peroxide or 2,2'-azo bis (3-methylpropionitrile) and preferably in the presence of an appropriate solvent such as toluene or dioxane at such temperature to allow adequate mixing of the reaction components above 25° C. and preferably between 30 and 100° C.; and (2) isolating the addition product comprising one anhydride group at each reaction site and hydrolyzing such group to yield the succinic acid side groups.

Another aspect of this invention deals with immobilizing, ionically, one or more basic bioactive agent to the carboxyl-bearing segmented copolyester to allow a timely release of such agents in the biological environment to support desirable pharmacological or cellular events—for example, anti-platelet, antiproliferative, antineoplastic, anticarcinogenic, antithrombotic, and/or anti-inflammatory agents. A more specific aspect of this invention deals with an absorbable coating or sealant comprising carboxyl-bearing, segmented copolyesters upon which is immobilized an antithrombotic agent such as dipyridamole. Another specific aspect of this invention deals with absorbable sealants or coatings for synthetic vascular grafts (including those made of polyurethanes, PET and E-PTFE) comprising segmented copolyesters of the types noted above, without being C-succinylated. Another aspect of this invention deals with a vascular graft sealant based on unsuccinylated and/or C-succinylated polyaxial segmented copolyester. Another aspect of the invention deals with sealants or coatings mixed with an ionic conjugate of a low-molecular weight (less than 10 kDa) C-succinylated polyaxial segmented copolyester or linear polyether-ester and a basic anticoagulant, antineoplastic, or antimicrobial drug. A specific aspect of this invention deals with a vascular graft sealant or coating comprising an ionic conjugate of a C-succinylated, segmented copolyester or polyether-ester from one of the groups noted above and a basic antithrombotic drug, such as dipyridamole mixed with an ionic conjugate of the same drug or a similar one that is linked to an absorbable low-molecular weight (less than 10 kDa) carboxyl-bearing copolyester that is preferably made by the copolymerization of trimethylene carbonate and ε-caprolactone in the presence of malic acid as the initiator. Alternatively, the latter sealant/coating can be mixed with a liquid conjugate made of a liquid C-succinylated copolymer and the basic drug wherein the polymer is produced by end-grafting a mixture of trimethylene carbonate and glycolide onto liquid polyethylene glycol. This invention also deals with a process for making the ionic conjugate which entails dissolving a specific polymer and the drug in a protonic solvent, such as hexafluoroisopropyl alcohol or trifluoroethanol, to obtain a true solution. The solvent can then be evaporated under reduced pressure to obtain the dry solid or liquid conjugate.

A more general aspect of this invention deals with absorbable coatings or sealants of conduit stabilizing stents and vascular devices, including vascular grafts and endovascular stent grafts, wherein said sealants or coatings comprise a segmented polyaxial copolyester, linear segmented polyether-ester, which may be C-succinylated and mixed with an ionic conjugate, which may be liquid at room temperature. The latter can be based on a low molecular weight C-succinylated polyaxial segmented copolyester or linear segmented polyether-ester. A specific aspect of this invention deals with a partially C-succinylated polyaxial segmented copolyester coating or sealant that is partially conjugated ionically with a bioactive agent including one of the following: antithrombotic (e.g., dipyridamole), antiangiogenic peptide (e.g., lanreotide) and an antimicrobial agent.

Another aspect of this invention deals with sealants or coatings containing a liquid ionic conjugate of a bioactive agent. This invention also deals with a bioactive agent that is held ionically and independently to both a liquid carboxyl-bearing absorbable or water-soluble polymeric additive and the solid matrix of said vascular graft sealant.

Described below are illustrative examples of the invention. It will be understood that these examples do not in any way constrain the scope of this invention. Modification to some, as appreciated by the artisan, are also contemplated.

EXAMPLE 1

Synthesis of Segmented Polyaxial Copolyester (PAX-I) using 21/30/4 (Molar) Caprolactone/Trimethylene Carbonate/Glycolide Copolymer as Triaxial Initiator and End-grafting with 40/5 Relative Molar Parts of l-Lactide/Caprolactone Glycolide (22.74 g, 0.2 mole), trimethylene carbonate (149.94 g, 1.47 mole), caprolactone (117.31 g, 1.03 mole), triethanolamine (1.34 g, 9 mmole), and stannous octanoate ($3.86 \times 10^{-4}$ mole as 0.2 M solution in toluene) were added under dry nitrogen atmosphere to 1.0 L resin kettle equipped with a mechanical stirrer. The reactants were melted at 85° C. under a nitrogen purge and then heated to 180° C. The formation of the polymeric initiator was completed after heating at 180° C. for 160 minutes. The product was cooled to room temperature and a mixture of l-lactide (282.24 g, 1.96 mole) and caprolactone (27.93 g, 0.25 mole) was added under nitrogen atmosphere. The reactants were heated to 85° C. under a nitrogen purge. And the final polymer formation was initiated after heating between 195 to 200° C. for 15 minutes until complete dissolution of the triaxial initiator. This was followed by heating for 23 hours at 140° C. The polymer was isolated, dried, and heated under reduced pressure to remove residual monomer. The polymer was purified by precipitating its methylene chloride solution in cold 2-propanol. The purified polymer was dried and characterized by NMR and IR (for identity), DSC for thermal transition ($T_m$=148° C.; ΔH=19 J/g) and inherent viscosity (I.V.) in chloroform for molecular weight (I.V.=1.14 dL/g).

EXAMPLE 2

Synthesis of Segmented Polyaxial Copolyester (PAX-II) using 26/26/4 (Molar) Caprolactone/Trimethylene Carbonate/Glycolide Copolymer as Triaxial Initiator and End-grafting with 40/4 Relative Molar Parts of l-Lactide/Caprolactone Using the monomer ratios noted above, the polymeric initiator was prepared and the end-grafting was conducted as described in Example 1 using proportional amounts of triethanolamine and stannous octanoate. The product was isolated and purified as described in Example 1. The purified polymer was characterized by NMR and IR (for identity), DSC for thermal properties ($T_m$=142° C.; ΔH=13 J/g), and molecular weight by GPC in methylene chloride ($M_n$=71 kDa; $M_w$=200 kDa).

EXAMPLE 3

Preparation of a Linear Segmented Polyether-ester

This was accomplished by first end-grafting poly(propylene glycol-b-ethylene glycol) having a molecular weight of 3300 Da (22.24 g, 6.74 mmole) with ε-caprolactone (117.42 g, 1.03 mole) and trimethylene carbonate (22.74 g, 0.196 mole) in the presence of stannous octanoate (0.385 mmole). The reaction was conducted at 180° C. for 2 hours in a mechanically stirred reactor under dry nitrogen atmosphere. To the reaction product l-lactide (282.18 g, 1.96 mole) and ε-caprolactone (27.92 g, 0.245 mole) were added at 120° C. The mixture was homogenized by stirring while heating (up to about 200° C.) for several minutes. The polymerization mixture was then cooled to 140° C., and the reaction was continued for 24 hours. The product was isolated and purified by precipitating its methylene chloride solution in cold 2-propanol. The solid product was isolated and dried under reduced pressure at 25, 40, and 80° C. until a constant weight is attained. The dry polyether-ester was characterized for identify (IR, NMR) thermal properties (DSC), and molecular weight (viscometry and GPC). It was shown to have the following properties: $T_m$=144° C.; ΔH=14 J/g; inherent viscosity=1.20 dL/g; $M_n$=87 kDa; $M_w$=157 kDa.

EXAMPLE 4

C-Succinylation of Polyether-ester

An aliquot of the polyether-ester from Example 3 (25 g) was dissolved in dry dioxane (150 mL) and mixed with benzoyl peroxide (360 mg) at 85° C. for 4 hours. The reaction product was cooled to 25° C. and precipitated in ice-water. The product was isolated and left at room temperature prior to drying until no residual anhydride groups were detected. The infra-red spectra of the dry sample was cast from a chloroform solution. The carboxylic acid-bearing C-succinylated product was then dried under reduced pressure at 25, 40, and 80° C. until a constant weight was obtained. The dry C-succinylated product was characterized for identity (IR, NMR), molecular weight (GPC), and thermal properties (DSC).

EXAMPLE 5

Preparation of Carboxyl-bearing Absorbable Lactide/Glycolide Copolyesters (PLG-C)

l-Lactide and glycolide were transferred under a dry nitrogen environment into a predried reactor equipped for mechanical stirring. A hydroxy acid initiator (e.g., malic or citric acid) was added to the monomer mixture at a monomer/initiator molar ratio that provided the desired molecular weight, each initiator molecule resulted in one polymeric chain. The polymerization charge was heated to about 110° C. until a liquid system formed. To this was added 0.2 molar solution of stannous octanoate catalyst at a monomer/catalyst molar ratio of 5000 to 10000. The polymerization mixture was heated at 160° C. for 15 hours or until all the monomer was practically consumed (as monitored by GPC). At the conclusion of the polymerization, the polymer was heated at 110° C. under reduced pressure to remove traces of unreacted monomer. The polymer was then characterized for identity (by IR) and molecular weight (using GPC in dichloromethane). A summary of the polymerization batch charge and scheme of typical polymers, and pertinent analytical data is provided in Table 1.

TABLE I

Preparation and Properties of Carboxyl-bearing Lactide/Glycolide Copolyesters

| Polymer | Monomer | Charge Mole | Charge Gm | Initiator[a] Type, M/I | Catalyst M/Cat[b] | Polymerization Conditions, Temp °C./ Time, Hr | GPC Data Mn, Da | Mw, Da | PDI |
|---|---|---|---|---|---|---|---|---|---|
| A | Lactide | 0.4 | 57.6 | Citric Acid, 10 | 4,500 | 160/1, 180/10 | 1,680 | 2,430 | 1.45 |
|  | Glycolide | 0.1 | 11.6 |  |  |  |  |  |  |
| B | Lactide | 0.4 | 57.6 | Citric Acid, 7.7 | 4,500 | 160/1, 180/12 | 1,420 | 1,950 | 1.37 |
|  | Glycolide | 0.1 | 11.6 |  |  |  |  |  |  |

[a]M/I = Molar ratio of monomer to initiator.
[b]M/Cat = molar ratio of monomer to catalyst.

EXAMPLE 6

Preparation of Carboxyl-bearing Copolyester Caprolactone/Glycolide (PCLG-C)

A mixture of ε-caprolactone (115.3 g), glycolide (6.17 g), and malic acid (28.53 g) were melt copolymerized using stannous octanoate as a catalyst (monomer/catalyst ratio=5000/1). The polymerization was conducted in a mechanically stirred reactor under dry nitrogen atmosphere by heating at 150° C. for 16 hours when practically all monomers were consumed. Traces of residual monomers were removed by evaporation under reduced pressure at 80° C. The resulting liquid polymer was shown by GPC to have an $M_n$=1290.

EXAMPLE 7

Preparation of PCLG-C Ionic Conjugate with Dipyridamole

An aliquot of PCLG-C was codissolved with the required amount of dipyridamole in trifluoroethanol (TFE) to provide an ionic conjugate where half of the carboxyl groups are neutralized with dipyridamole. The ionic conjugate was obtained by evaporating TFE under reduced pressure at 25° C. until a constant weight is attained.

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. An absorbable sealant for biomedical devices comprising a segmented copolyester having a molecular weight of more than 5 kDa, a glass transition temperature of less than 35° C., and low degree of crystallinity evidenced by a heat of fusion of less than 25 J/g, the segmented copolyester made by a process comprising the steps of:
    reacting a mixture of trimethylene carbonate, caprolactone, and glycolide with a polyhydroxy initiator, thereby forming an amorphous, polyaxial polymeric initiator; and
    end-grafting a mixture of caprolactone and lactide onto the polyaxial initiator.

2. An absorbable sealant as set forth in claim 1 wherein the biomedical devices are selected from synthetic vascular grafts, endovascular stent grafts, and conduit stabilizing stents.

3. An absorbable sealant as in claim 1 wherein the segmented copolyester further comprises pendant carboxyl-bearing side groups.

4. An absorbable sealant as in claim 3, wherein the process for making the carboxyl-bearing, segmented copolyester comprises the further steps of:
    reacting the segmented copolyester with maleic anhydrid under free-radical conditions, thereby introducing at least one anhydride group per chain; and
    hydrolyzing the anhydrid-bearing copolyester, thereby forming succinic acid based side groups.

5. An absorbable sealant as in claim 3 wherein the segmented copolyester is ionically conjugated with a basic bioactive agent.

6. An absorbable sealant as in claim 5 wherein the basic bioactive agent comprises an antithrombotic drug.

7. An absorbable sealant as in claim 5 wherein the bioactive agent is an antimicrobial compound.

8. An absorbable sealant as in claim 5 wherein the bioactive agent is an antiproliferative compound.

9. An absorbable sealant as in claim 1 further comprising at least one bioactive agent selected from the group consisting of anticoagulant agents, antiproliferative agents, antithromibotic agents, anti-inflammatory agents, antineoplastic agents, antiangiogenic agents, and antibiotic agents.

* * * * *